US006398408B1

(12) United States Patent
Polkus

(10) Patent No.: US 6,398,408 B1
(45) Date of Patent: Jun. 4, 2002

(54) AUTOMATED IMAGE CHAIN GEOMETRIC QUANTIFICATION

(75) Inventor: Vincent S. Polkus, Delafield, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/732,046

(22) Filed: Dec. 7, 2000

(51) Int. Cl.[7] .............................................. G01D 18/00
(52) U.S. Cl. ...................... 378/207; 378/163; 378/205
(58) Field of Search ................................. 378/162, 163, 378/164, 207, 205

(56) References Cited

U.S. PATENT DOCUMENTS 3,714,428 A * 1/1973 Gasaway ................. 378/163
5,917,877 A * 6/1999 Chiabrera et al. ........... 378/5.3
6,206,566 B1 * 3/2001 Schuetz ..................... 378/205

\* cited by examiner

*Primary Examiner*—Robert H. Kim
*Assistant Examiner*—Allen C. Ho
(74) *Attorney, Agent, or Firm*—McAndrews, Held & malloy, Ltd.; Peter J. Vogel; Michael A. Dellapenna

(57) ABSTRACT

An x-ray imaging machine (10) is calibrated by placing a phantom (30) between an x-ray tube (20) and an x-ray detector (310). The phantom causes a first dimension $D_{1,d}$ and a second dimension $D_{2,d}$ to be projected onto the detector. From the projected dimensions and a physical dimension of the phantom (t), a processor (302) calculates the focal distance (FD) of the machine, the source image distance (SID) of the machine, and the object-to-detector distance (ODD).

16 Claims, 2 Drawing Sheets

AUTOMATED IMAGE CHAIN GEOMETRIC QUANTIFICATION

BACKGROUND OF THE INVENTION

This invention relates to x-ray system calibration, and more particularly relates to calibration of positional relationships among key components of an x-ray imaging machine.

The controlled delivery of x-rays on a diagnostic imaging system requires specific knowledge of the geometry, orientations, and positional relationships among the key components of the image chain. In order to collimate the x-ray beam, it is necessary to know the source to image distance (SID) as well as the actual size of the receptor that the beam is to be projected onto. Other parameters, such as the object-to-detector distance (ODD), are often required for computations involving automatic tracking of the tube and detector. The incorporation of these parameters in the control algorithms for the system may be accomplished in a variety of ways, including direct entry for situations where the geometry is fixed or by some form of calibration in cases where the geometry is variable or where component production tolerances could contribute to system performance variation. On film-based image systems, this calibration may involve taking direct measurements of the positioner and entering these into the system database or indirect means using x-ray images where certain dimensional data from the images are then entered into the system database. Both of these approaches involve a manual process that may result in non-repeatable outcomes. This problem is addressed by this invention, and a solution is provided.

BRIEF SUMMARY OF THE INVENTION

The preferred embodiment is useful in an x-ray imaging machine including an x-ray tube generating x-rays from a focal spot. The x-ray field contains a central axis or ray, and the machine includes a detector of the x-rays defining a source image distance measured parallel to the central axis between said focal spot and said detector. The machine also includes collimator blades defining a blade plane and defining a focal distance measured parallel to the central axis between the focal spot and the blade plane. In such an environment, the machine may be calibrated by providing a phantom positioned between the detector and the x-ray tube. The phantom comprises a first portion defining a first dimension that generates on the detector a first x-ray image that defines a first projected dimension. The phantom also comprises a second portion defining a second dimension that generates on the detector a second x-ray image that defines a second projected dimension. A predetermined distance measured parallel to the central axis separates the first and second portions. A processor is responsive to the first projected dimension or the second projected dimension to calculate at least one of the focal distance and the source image distance.

Another embodiment also useful in the above-described environment comprises a method including positioning a phantom between the detector and the x-ray tube. The phantom comprises a first portion defining a first dimension and comprises a second portion defining a second dimension. A predetermined distance measured parallel to the central axis separates the first and second portions. A first x-ray image is generated on the detector in response to said first portion. The first x-ray image defines a first projected dimension. A second x-ray image is generated on the detector in response to said second portion. The second x-ray image defines a second projected dimension. At least one of said focal distance and said source image distance is calculated in response to the first projected dimension or the second projected dimension.

By using the foregoing techniques, an x-ray machine may be calibrated with a degree of convenience and accuracy previously unavailable. For example, eliminating the direct measurement of physical sizes and entering these values into the system database improve the consistency of the final system calibration. In this way, system performance and system-system performance consistency both are improved. In addition, long-term system quality is improved since a calibrated ODD value would be system specific and immune to error if the physical system configuration changes without a corresponding software database change.

DETAILED DESCRIPTION OF THE INVENTION

The preferred embodiment uses recognized geometric relationships to compute system parameters. More specifically, the preferred embodiment incorporates direct digital size information from the system upon which to base the computations. In one form, the acquired images may be presented to a trained service operator with instructional information to invoke a measurement algorithm for the two projected shapes from the calibration apparatus or the system may incorporate a pattern recognition system to automatically compute the required inputs to the geometric formulae.

Figure 1:
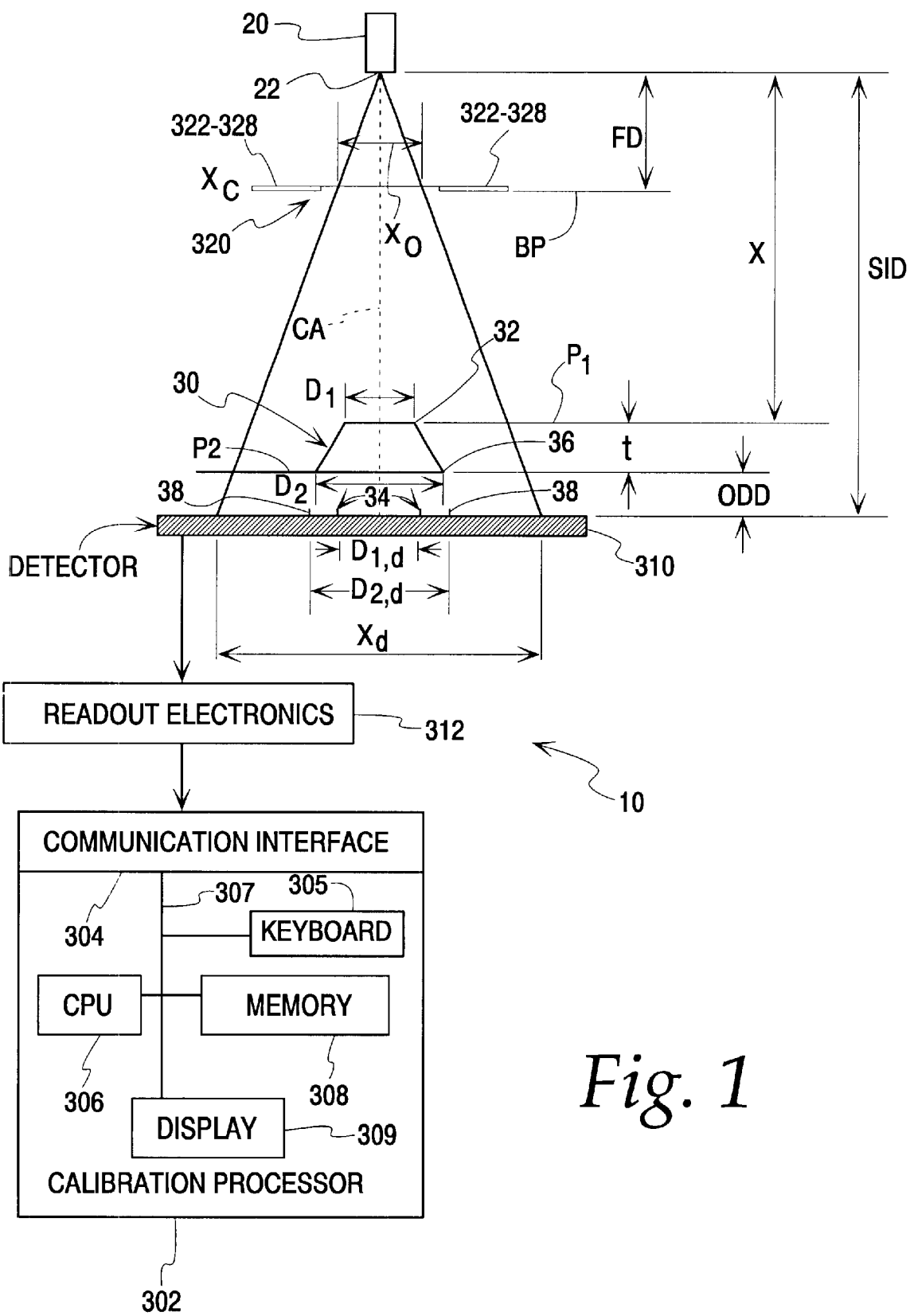
FIG. 1 is a schematic, fragmentary side elevational view of a preferred form of certain mechanical aspects of the invention and is a schematic block diagram of a preferred form of certain electrical aspects of the invention.

In general, the preferred embodiment includes a system calibration process whereby image system geometric factors, such as source-to- image distance (SID), object-to-detector distance (ODD), and the collimator blade focal distance (FD) are computed based upon measurements obtained from the digital image detector. To obtain these parameters, two radiographic exposures are taken at different levels of collimation at a fixed SID with a geometric apparatus, such as a phantom, in the beam of know proportions. For illustrative purposes, the device is depicted as a conical phantom, but the device may use two known geometric shapes and associated dimensional criteria existing on different planes that are oriented perpendicular to the central ray defined by the x-ray beam. FIG. 1 shows the basic configuration in relationship to an exemplary x-ray image system. The preferred embodiment utilizes the shape sizes that are projected onto the digital detector image plane and the overall field size boundaries to computer the geometric parameters.

Referring to FIG. 1, a preferred form of x-ray imaging machine 10 made in accordance with the invention comprises an x-ray tube 20 that generates x-rays from a focal spot 22 and directed in relationship to a central axis CA. A digital image detector 310 detects the x-rays in a well-known manner. The distance parallel to axis CA between focal spot 22 and detector 310 defines a source image distance (SID). A collimator 320 includes collimator blades 322–328, shown schematically in FIG. 1, that define a blade plane BP. A focal distance (FD) is measured parallel to axis CA between focal spot 22 and blade plane BP.

Figure 2:
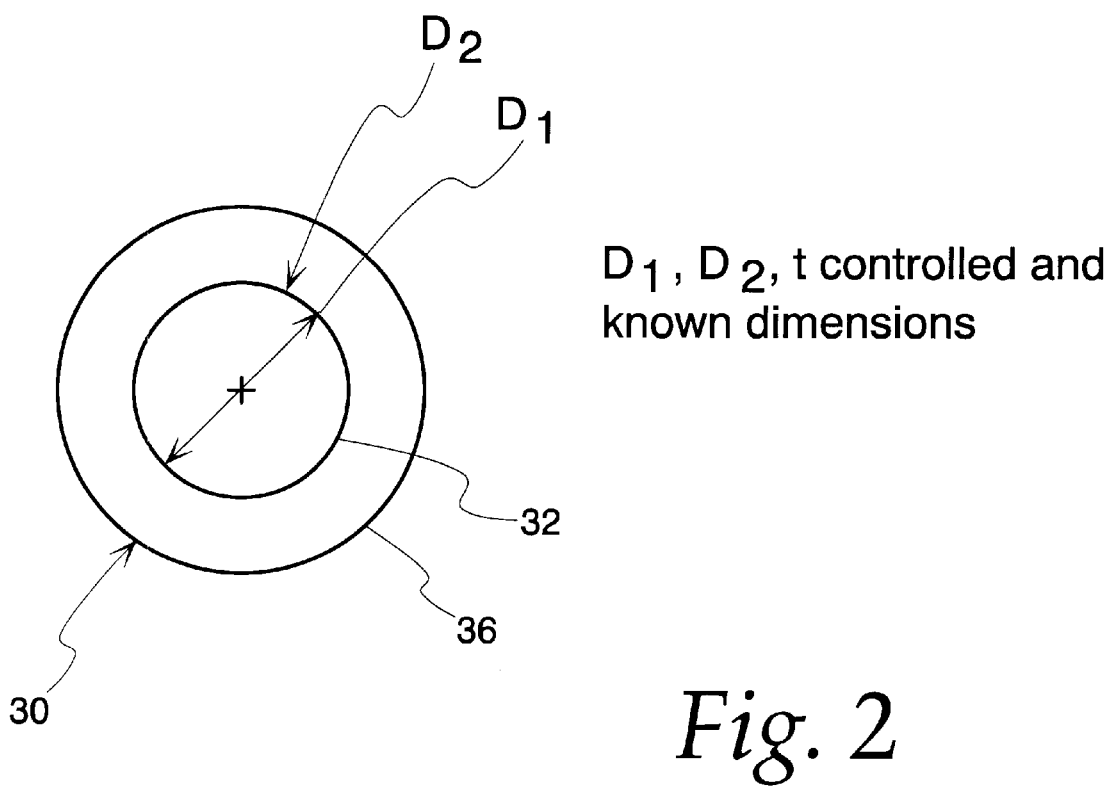
FIG. 2 is a top plan view of a portion of the mechanical aspects shown in FIG. 1.

Referring to FIGS. 1 and 2, a phantom 30, shaped like a truncated cone, includes a first portion 32 comprising a circular top surface defining a diameter dimension $D_1$ and lying in a plane P1 perpendicular to the central axis CA. Portion 32 projects an image 34 onto detector 310 defining a diameter dimension $D_{1,d}$. A second portion 36 comprising a circular bottom surface defining a diameter dimension $D_2$ and lying in a plane P2 perpendicular to the central axis CA. Portion 36 projects an image 38 onto detector 310 defining a diameter dimension $D_{2,d}$. Of course, dimensions or geometric attributes other than diameters can be used to implement the invention. The phantom only needs to be shaped to project whatever type of dimension is used. A distance t measured parallel to axis CA separates portions 32 and 36. Portion 36 is separated from detector 310 by a distance ODD measured parallel to axis CA.

Referring to FIG. 1, a calibration processor 302 includes communication interface 304, a keyboard 305, a central processing unit (CPU) 306, a memory 308 and a display unit 309, such as a computer monitor, 309 all coupled by a bus 307 as shown. Signals indicating the projected dimensions are read from detector 310 by readout electronics 312. The design and operation of most of the components with numbers greater than 300 are described in more detail in application Ser. No. 09/342,686, filed Jun. 29, 1999, now U.S. Pat. No. 6,215,853 in the names of Kenneth S. Kump et al., entitled "Apparatus And Method For x-ray Collimator Sizing And Alignment," assigned to General Electric Company and incorporated by reference in its entirety into this specification.

In order to calibrate machine 10, the dimensions t, $D_1$ and $D_2$ are input to processor 302 through keyboard 305. In response to the images defining dimensions $D_{1,d}$ and $D_{2,d}$, processor 302 makes the following calculations:

$$\frac{X+t+ODD}{X_d} = \frac{FD}{X_o}$$

$$\frac{X}{D_1} = \frac{X+t+ODD}{D_{1,d}}$$

$$\frac{X+t}{D_2} = \frac{X+t+ODD}{D_{2,d}}$$

where $D_{1,d}$ and $D_{2,d}$ are the projected dimensions of the radiopaque shapes that are contained within the calibration apparatus. Using these relationships enables a relationship for X and ODD $$X = \left[\frac{D_{2,d}/D_2}{\left(\frac{D_{1,d}}{D_1} - \frac{D_{2,d}}{D_2}\right)}\right]t$$

$$ODD = D_{1,d}\left(\frac{X}{D_1}\right) - X - t$$

Within the scope of the invention, the shape projections into the detector plane—$D_{1,d}$ and $D_{2,d}$—the values may be obtained using an established pattern recognition algorithm which would then invoke a measurement routine or scale measurements performed by the operator on a digital workstation on that is a part of the system.

Solving for the collimator blade opening for the initial exposure yields $$X_o^1 = X_d^1\left(\frac{FD}{X+t+ODD}\right)$$

For the second exposure the system computes the change in position for the collimator blades such that $$X_o^2 = X_o^1 + \Delta X$$

and since $$X_o^2 - X_o^1 = \left(\frac{FD}{X+t+ODD}\right)(X_d^2 - X_d^1) = \Delta X$$

$$FD = \Delta X\left[\frac{X+t+ODD}{X_d^2 - X_d^1}\right]$$

Changing the collimator blade opening can be accomplished in the manner described in the application incorporated by reference. The above formulation demonstrates that it is feasible for the system to compute the geometric parameters related to image system geometry utilizing two exposures at different levels of collimation.

The computed values are displayed on display 309.

Those skilled in the art will recognize that the preferred embodiments may be altered and modified without departing from the true spirit and scope of the invention as defined in the accompanying claims.

What is claimed is:

1. In an x-ray imaging machine including an x-ray tube generating x-rays from a focal spot, said x-rays including a central axis, said machine including a detector of the x-rays defining a source image distance measured parallel to said central axis between said focal spot and said detector and including collimator blades defining a blade plane and defining a focal distance measured parallel to the central axis between the focal spot and the blade plane, apparatus for calibrating the machine comprising:

a phantom positioned between the detector and the x-ray tube, said phantom comprising a first portion defining a first dimension that generates a first x-ray image on the detector, said first x-ray image defining a first projected dimension, said phantom comprising a second portion defining a second dimension that generates a second x-ray image on the detector, said second x-ray image defining a second projected dimension, said first and second portions being separated by a predetermined distance measured parallel to said central axis; and a processor responsive to the first projected dimension or the second projected dimension to calculate at least one of said focal distance and said source image distance.

2. Apparatus, as claimed in claim 1, wherein said processor calculates both said focal distance and said source image distance.

3. Apparatus, as claimed in claim 1, wherein the processor further calculates an object distance measured parallel to the central axis between the first portion and the detector or between the second portion and the detector.

4. Apparatus, as claimed in claim 3, wherein the object distance is measured between the second portion and the detector and wherein the second portion is located closer to the detector than the first portion.

5. Apparatus, as claimed in claim 1, wherein the first dimension is smaller than the second dimension and wherein the first projected dimension is smaller than the second projected dimension.

6. Apparatus, as claimed in claim 1, wherein the first portion defines a first diameter and the second portion defines a second diameter larger than the first diameter.

7. Apparatus, as claimed in claim 1, wherein the first portion lies in a first plane perpendicular to the central axis and wherein the second portion lies in a second plane perpendicular to the central axis.

8. Apparatus, as claimed in claim 1, wherein the detector comprises a digital image detector.

9. In an x-ray imaging machine including an x-ray tube generating x-rays defining from a focal spot, said x-rays defining a central axis, said machine including a detector of the x-rays defining a source image distance measured parallel to said central axis between said focal spot and said detector and including collimator blades defining a blade plane and defining a focal distance measured parallel to the central axis between the focal spot and the blade plane, a method of calibrating the machine comprising:

positioning a phantom between the detector and the x-ray tube, said phantom comprising a first portion defining a first dimension and comprising a second portion defining a second dimension, said first and second portions being separated by a predetermined distance measured parallel to said central axis;

generating a first x-ray image on the detector in response to said first portion, said first x-ray image defining a first projected dimension;

generating a second x-ray image on the detector in response to said second portion, said second x-ray image defining a second projected dimension;

calculating at least one of said focal distance and said source image distance in response to the first projected dimension or the second projected dimension.

10. A method, as claimed in claim 9, wherein said calculating comprises calculating both said focal distance and said source image distance.

11. A method, as claimed in claim 9, wherein said calculating comprises calculating an object distance measured parallel to the central axis between the first portion and the detector or between the second portion and the detector.

12. A method, as claimed in claim 11, wherein the object distance is measured between the second portion and the detector and wherein the second portion is located closer to the detector than the first portion.

13. A method, as claimed in claim 9, wherein the first dimension is smaller than the second dimension and wherein the first projected dimension is smaller than the second projected dimension.

14. A method, as claimed in claim 9, wherein the first portion defines a first diameter and the second portion defines a second diameter larger than the first diameter.

15. A method, as claimed in claim 9, wherein the first portion lies in a first plane perpendicular to the central axis and wherein the second portion lies in a second plane perpendicular to the central axis.

16. A method, as claimed in claim 9, wherein the detector comprises a digital image detector.

* * * * *